April 26, 1955 A. TOTH Plant Pat. 1,387
DWARF DOGWOOD PLANT
Filed April 19, 1951
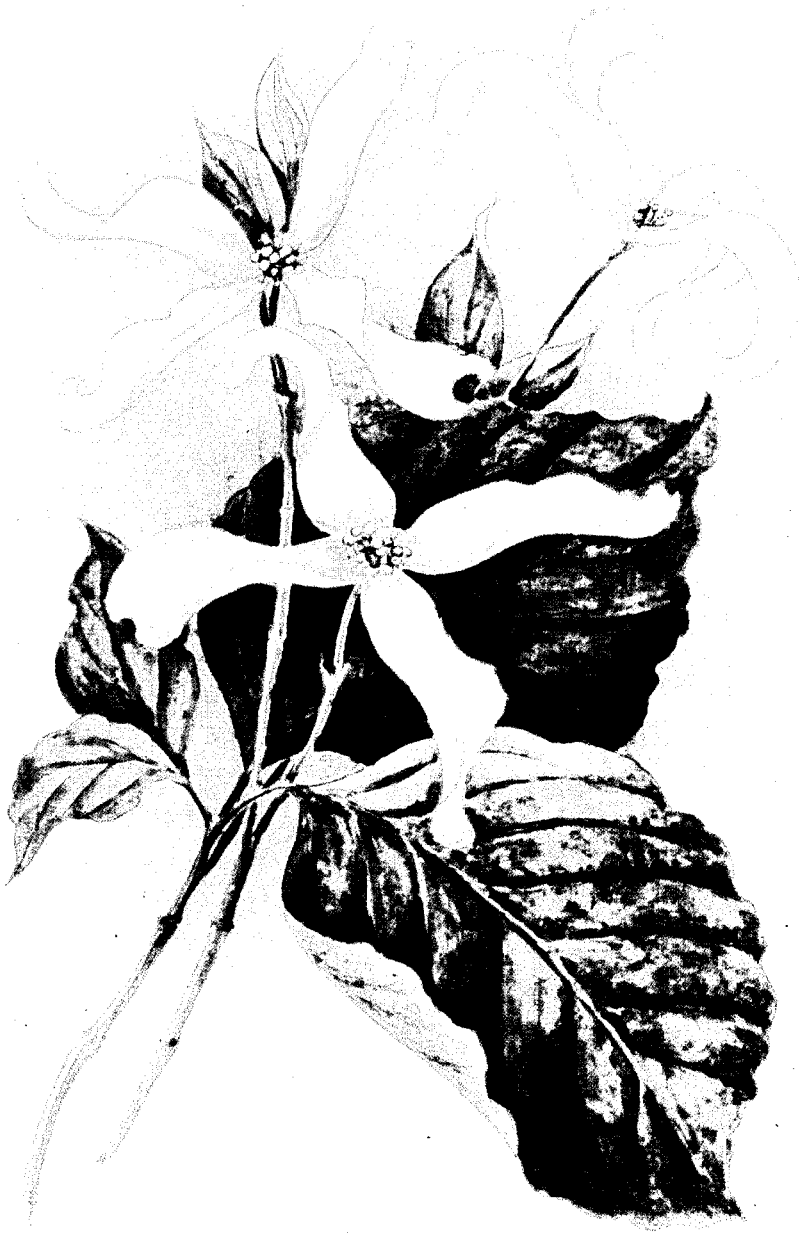
WITNESS
Addison E. Avery
INVENTOR
ALEX TOTH,
BY Justus E. Macklin
ATT'Y.

United States Patent Office

Plant Pat. 1,387
Patented Apr. 26, 1955

1,387

DWARF DOGWOOD PLANT

Alex Toth, Madison, Ohio

Application April 19, 1951, Serial No. 221,893

1 Claim. (Cl. 47—60)

This invention relates to a novel and distinct variety of dwarf dogwood.

This new variety of dogwood plant was originally discovered growing as a seedling among other plants then being asexually reproduced by me. The foregoing other plants had for the most part grown to six or seven feet in height. This instant variety is much smaller. Upon being further asexually reproduced, this new plant developed into the novel and distinct variety of dwarf dogwood with the definite, unusual and heretofore unknown characteristics, herein described and shown.

This new variety of dogwood may be considered a variety of *Cornus florida* of the genus Cornus sometimes called Cynoxylon. It has been asexually reproduced by budding with seedlings of a common variety of *Cornus florida,* which had been planted as seedlings in the usual nursery rows. The plants from these seedlings of *Cornus florida* have been budded with buds from my new variety of dwarf dogwood which are allowed to grow until large enough for replanting.

The principal reproduction prior to the present application was in Madison, Lake County, Ohio. Both the genus and species are indigenous to the temperate zone in the northern part of the United States.

The growth at the end of the second summer has been up to between eight and fifteen inches. At the end of eight to ten years the new variety of dwarf dogwood will have reached the height of about four feet. The full height is not yet determined.

The leaves are large and contain a predominance of dark green.

The four bracts are large. They are cream colored and have a reddish-purple tip spot.

The flowers have the appearance of clustered brownish-yellow small green pods.

The distinctive colorings of the leaves of the plant according to the Maerz & Paul Dictionary of Color may be described as follows:

The leaf is mottled, with its principal color corresponding to that of Maerz & Paul Plate No. 22–L–9. The back of the mature leaf corresponds to Plate No. 20–D–4.

The long slender bracts are principally of a cream color, corresponding to Plate No. 9–D–1.

The tip of the bracts is reddish-purple, the color corresponding essentially to Plate No. 54–K–2.

The newer or smaller leaves as appearing at the left of the drawing are of lighter green than the large leaves.

As shown in the drawings, the flowers at their outer portions are, as indicated, a brown shaded toward yellow near the green inner portions. Thus, the outer portion of the flower may be designated as a brown, approximately that of Plate No. 11–A–11, and on some flowers approximately 11–8–G. The green inner portions correspond approximately to Plate No. 27, ranging from 7A to C.

The drawing illustrates many of the characteristics not found in parent stock nor in any other known varieties. These characteristics greatly increase its beauty and add to the value of the plant.

Having now fully shown and described my new variety of dwarf dogwood plant and the mode of its production, what I claim and desire to secure by Letters Patent of the United States is:

A new and distinct variety of dogwood plant, of the species *Cornus florida,* as described and illustrated, and characterized by having long, slender bracts mainly of a cream color with reddish-purple tips, the flower having the appearance of brownish-yellow tips on small green pods, and the leaves being large and predominantly dark green.

No references cited.